United States Patent [19]

Woronowicz

[11] 4,258,428
[45] Mar. 24, 1981

[54] COMPTON EFFECT DEEMPHASIZER FOR GAMMA CAMERAS

[75] Inventor: Eric M. Woronowicz, West Allis, Wis.

[73] Assignee: General Electric Company, Schenectady, N.Y.

[21] Appl. No.: 52,040

[22] Filed: Jun. 25, 1979

[51] Int. Cl.³ .............................................. G01T 1/20
[52] U.S. Cl. .................... 364/527; 364/525; 364/414; 250/363 S; 250/369
[58] Field of Search ............... 364/525, 527, 515, 521, 364/414, 518; 250/363 S, 369

[56] References Cited

U.S. PATENT DOCUMENTS

| | | | |
|---|---|---|---|
| 3,011,057 | 11/1961 | Anger | 250/363 S |
| 3,666,952 | 5/1972 | McCready et al. | 250/363 S |
| 3,697,753 | 10/1972 | Martone et al. | 250/363 S |
| 3,732,419 | 5/1973 | Kulberg et al. | 250/363 S |
| 3,919,556 | 11/1975 | Berninger | 250/363 S |
| 3,942,011 | 3/1976 | Stout | 250/363 S |
| 3,980,886 | 9/1976 | Stout | 250/363 S |
| 4,071,762 | 1/1978 | Lange et al. | 250/363 S |
| 4,179,607 | 12/1979 | Lange et al. | 250/363 S |

Primary Examiner—Charles E. Alkinson
Assistant Examiner—Gary Chin
Attorney, Agent, or Firm—Ralph G. Hohenfeldt

[57] ABSTRACT

A gamma camera having a Compton scattered radiation deemphasizer. A summing device produces pulses proportional to the total energy of each scintillation caused by absorption of gamma photons in a scintillation crystal. Scintillation events are displayed at the x,y coordinates of the event on a cathode ray tube screen by unblanking the tube with z pulses applied to its control electrode. The deemphasizer determines where the peaks of total energy pulses fall in a part of the energy spectrum or window and between lower and upper limits. The deemphasizer causes small z pulses to be produced in the part of the spectrum where Compton scatter is most prevalent and causes increasingly larger z pulses as total energy increases to the midpoint of the spectrum where Compton scatter is insignificant. Constant amplitude z pulses are produced at and after the midpoint.

7 Claims, 7 Drawing Figures

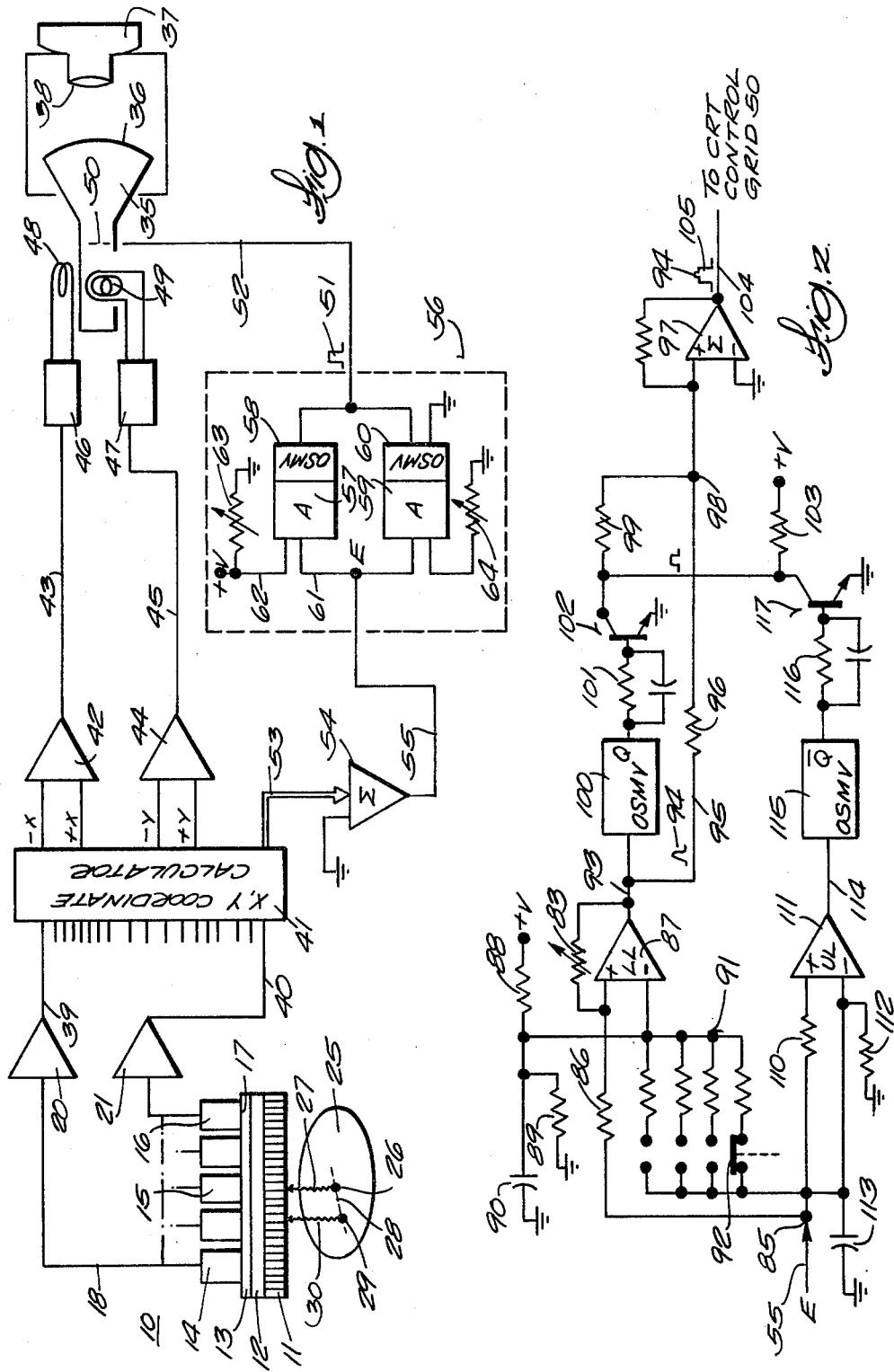

COMPTON EFFECT DEEMPHASIZER FOR GAMMA CAMERAS

This invention relates to scintillation camera systems or, as they are commonly called, gamma camera systems. More specifically, the invention relates to apparatus for reducing the effect of Compton scattered radiation which, in existing camera systems, is a significant cause of poor image definition.

The invention is applicable to various gamma camera systems and is exemplified in the well-known Anger system disclosed in U.S. Pat. No. 3,011,057. Gamma ray cameras of this type are used in nuclear medicine to detect gamma radiation or other high energy photons emitted from a body in which a radioisotope has been infused. The quantity of gamma ray photons emitted depends upon the quantity of isotope which is absorbed by the tissue in a body organ under examination. The emitted gamma ray photons are absorbed in a plate of crystalline material and a scintillation occurs at the point of absorption. Most of the points of absorption in the crystal have substantially the same x and y coordinates as the point in the body from which the gamma ray photon is emitted, since the photons are directed to the scintillation crystal with a collimator that eliminates most photons which are in an angular course toward the scintillation crystal. An array of photomultiplier (PM) tubes, generally hexagonally arranged, are optically coupled to the crystal so that each tube will produce an output pulse signal whose magnitude depends on the particular geometrical relationship of the tube to the scintillation events being detected. Each PM tube has an x and y coordinate. The signals from each tube are supplied to a position calculator, generally a resistor weighting matrix which uses the simultaneous pulse signals from each tube to compute the x and y coordinates of each scintillation event. The x and y coordinate signals are used to drive the deflection coils of a cathode ray tube or similar display. Conventionally, the energies of all PM tube pulses for each scintillation event are summed to produce a total energy signal which is subjected to pulse height analysis. If the total energy falls within the window of the analyzer, a z pulse is produced which unblanks the cathode ray tube display to write a light spot on the display screen at the calculated x,y coordinates of the event. Usually a photographic film is used as an integrator of the large number of points or spots of light appearing on the screen of the display. When a substantial number of scintillation events are integrated, the points define the image of the organ in which the gamma ray emitting isotope is infused.

In prior art apparatus, every pulse representative of total energy of a scintillation event and which falls between the upper and lower level limits of the discriminator window causes a z pulse to be formed which unblanks the cathode ray tube so that a light point or spot is written on the screen. Traditionally, all z pulses have the same amplitude and, hence, drive the cathode ray tube to equal brightness so that all points are of equal brightness regardless of the energy of the pulse.

Unfortunately, all of the gamma ray photons that pass through the collimator to the crystal to cause a scintillation event are not necessarily congruent with the point in the body tissue where an atom of the isotope emitted the gamma ray photon. Gamma ray photons can, of course, be emitted in any direction from the infused organ into parts of the body without being propagated toward the camera collimator. Some of these misdirected photons and, even photons that start out originally on a course toward the collimator, pass close to or actually collide with atoms in body tissue, air or collimator where they undergo a change of momentum and a change in direction or shift which may aim them through the collimator. This is the classical Compton modified scattering process.

The Compton scattered gamma ray photons, although actually laterally displaced from the point at which they originated in the body, pass through the collimator and are detected in alignment with wherever they emerged from the body. When these photons are absorbed in the scintillation crystal they cause a z pulse to be generated and a point of light to be written on the display screen at coordinates which do not agree with the coordinates of the point in the body at which the photon was emitted. These points are integrated from the screen by the photographic film as if they were valid and give the image integrating photographic film a hazy appearance. The photons which have undergone Compton scattering are mostly on the low energy side or near the lower level of the energy window of the pulse height analyzer.

SUMMARY OF THE INVENTION

In accordance with the invention, scintillation events that are due to Compton scattering are suppressed or deemphasized compared to other higher energy events. Briefly stated, the invention is characterized by feeding the voltage pulses whose amplitudes correspond with the total energy in each scintillation event to a comparator whose threshold is set to correspond with the lower level or limit of the discriminator window. The output of the comparator is a pulse or peak whose amplitude depends on the energy of the input pulse. Any output signal from the comparator also triggers a one-shot multivibrator which produces a z pulse for every incoming accepted total energy pulse. The pulse from the comparator, whose amplitude depends on how much the total energy is above threshold level, is added to the z pulse.

In the low energy range of the window, a substantial amount of Compton scattered low energy radiation is present. Hence, near the lower level of the discriminator window, little signal from the threshold comparator is added to the basic z pulse signal. Any incoming total energy pulses, however, which are quite energetic and progressively closer to peak energy region of the window cause progressively more signal to be added to the basic z pulse until the peak is reached at which time the comparator amplifier becomes saturated and the z pulse reaches its maximum amplitude. Thus, it is only the gamma photons which are near, at or above peak energy which write a point on the screen that is at maximum brightness. Photons which have energies just above the lower window level are likely to be in a region of the energy spectrum where significant Compton scattered photons are present so the output pulse from the threshold comparator will be relatively small and these events will not add much to the basic z pulse. Hence, they result in a near minimum brightness spot being written on the display screen and the effect of Compton scattered radiation is deemphasized.

A more detailed description of an illustrative embodiment of the invention will now be set forth in reference to the drawings.

DESCRIPTION OF THE DRAWINGS

FIG. 1 is a block diagram of a gamma camera system which is substantially conventional but in which the new Compton scattered radiation deemphasizer can be used;

FIG. 2 is a diagram of the essential parts of a circuit for accomplishing Compton scattered deemphasis;

DESCRIPTION OF A PREFERRED EMBODIMENT

Figure 3:
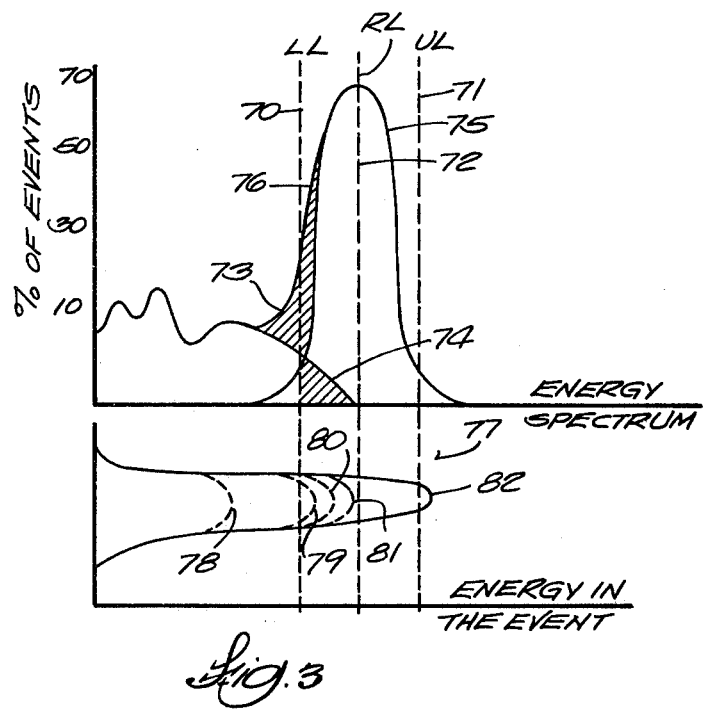
FIG. 3 is a graph comprised of upper and lower parts, the upper part being a plot of the photon energy spectrum intercepted by the gamma camera versus the percentage of scintillation events that are likely to have a particular energy and, the lower part being a plot of voltage pulses which are proportional to the total energies in different scintillation events.

A substantially conventional gamma camera system in which the new scattered radiation deemphasizer can be incorporated is shown schematically in FIG. 1. At the far left there is a conventional gamma camera which is generally designated by the reference numeral 10. This is an Anger type camera comprised of a collimator 11, a scintillation crystal disk 12, a glass plate 13 and several photomultiplier (PM) tubes such as those marked 14, 15 and 16 which have their light input ends or faces 17 resting on the top surface of plate 13. Plate 13 couples scintillation events or light flashes which occur in crystal 12 due to absorption of gamma photons to the input faces 17 of the PM tubes. Gamma camera 10, like most gamma cameras now in use, may have the typical 19 or 37 PM tubes arranged in circles around central PM tube 15. Every scintillation occurring in crystal 12 is sensed by each PM tube and each tube produces an output pulse whose amplitude depends upon the location of the particular tube with respect to the scintillation event in the crystal. An output line such as those marked 18 and 19 on PM tubes 14 and 16, respectively, leads from each PM tube to an individual preamplifier. Two of the preamplifiers are shown and are marked 20 and 21. How the signals from the preamplifiers are processed in the circuit will be discussed later.

A body undergoing gamma ray imaging is located below collimator 11 and is marked 25. Assume that some tissue or an organ of this body has been infused with a radioisotope. A thyroid gland is a typical organ that is examined by this method. Assume that a radioactive disintegrate occurs in this gland at the place marked 26. Normally and desirably a large number of such emissions will result in gamma rays being projected toward the collimator as indicated by the arrowheaded line marked 27. Such gamma ray photons which are aligned with the collimator will go straight through it and be absorbed at a point in the scintillation crystal 12 and a scintillation or light flash will occur at the point of absorption. The scintillation will be detected and, ultimately, its position will be determined as having the same coordinates as point 26 in the body. Radioactive disintegrations, of course, yield gamma ray photons which may go off in any direction and not pass through collimator 11. A gamma ray photon, for example, originating at point 26 may head in the direction of the dashed arrowheaded line 28 and interact with electrons of an atom at point 29, for instance, in which case the gamma ray photon will lose energy and change direction and may follow a path indicated by the arrowheaded line 30 to the collimator. This is Compton scattering. The camera senses the Compton scattered photon which caused this scintillation event as coming from point 29 instead of its true originating point 26. If the photon still falls within the acceptable energy range or window, the cathode ray tube will be unblanked to produce a light spot at x,y coordinates where the photon seems to have come from and image resolution is degraded.

In the right region of the FIG. 1, the image display device is shown. It comprises a cathode ray tube 35 which has a phosphor screen 36. As will be discussed in greater detail, each time a scintillation event corresponding with a gamma ray photon having sufficient energy to be accepted is detected, the electron beam of the cathode ray tube is unblanked and a light spot is generated on screen 36 at x and y coordinates corresponding with the x and y coordinates of the scintillation event in the crystal, and desirably, with the coordinates of the point in the body from which the photon originated. These successively ocurring light spots are integrated by the film in an enclosed camera 37 whose lens 38 is pointed at screen 36. As is well-known, if the integration time is long enough, enough points will be developed to define the image of the radioisotope infused organ on the film. However, as previously exlained, some light spots will also be generated at points outside of the true image of the infused organ because of Compton scatter.

The conventional method of calculating the x,y coordinates of each scintillation event in the crystal, the manner in which gamma photons of unacceptable energies are discriminated against and the manner in which z pulses for unblanking the cathode ray tube are generated will now be described in the conventional system depicted in FIG. 1.

As previously stated, the different amplitude output signals from the PM tubes are fed to the inputs of preamplifiers such as those marked 20 and 21. Each scintillation event is viewed or detected by each PM tube and the amplitudes of their output signals depend on their distance and geometrical relationship with respect to the scintillation event in the crystal and on the gamma ray photon energy. In the present system, the signals on the various output lines 39 and 40 from the peramplifiers are fed to an x,y coordinate calculator which is generally designated by the numeral 41. This calculator may comprise a weighting resistor matrix, not shown, usually composed of four resistors in each channel whose values are proportional to the x and y distances of the tube from the central PM tube in the array. As is well-known, these signals are combined in such a way as to produce a net signal corresponding with the $-x$ and $+x$ coordinates and the $-y$ and $+y$ coordinates for a scintillation. The $+x$ and $-x$ coordinate signals are inputted to a summing amplifier such as the one marked 42 where they are combined to form a signal on output line 43 whose amplitude is representative of the x coordinate position of the scintillation. Similarly, the +y and −y signals are summed in a summing amplifier 44 and the amplitude of the output signal on line 45 is representative of the y coordinate of the scintillation event. The x and y coordinate signals are supplied to x and y deflection signal amplifiers 46 and 47, respectively. The output signals from the deflection amplifiers are supplied to horizontal and vertical magnetic deflection coils 48 and 49, respectively, of cathode ray image display tube 35.

Even though the x and y coordinates for substantially every scintillation event are calculated, the cathode ray tube is only unblanked to produce a light spot on its screen if the scintillation event resulted from a gamma ray photon having an energy falling within the upper and lower limits of a window-type discriminator that is in the dashed line rectange 56 in FIG. 1. The unblanking or brightness modulation grid 50 of the cathode ray tube normally has a potential on it which biases the electron beam of the tube off. For scintillation events which have sufficient energy, however, z pulses such as the one marked 51 are outputted by discriminator 56 and are supplied over line 52 to control grid 50 to thereby unblank the tube and produce a light spot at the calculated x and y coordinates on the display screen 36.

The z pulse forming circuit originates at the x,y coordinate calculator 41. For every scintillation event, the pulses from all of the PM tubes are delivered by way of a cable 53 to the input of a summing amplifier 54. Thus, the output pulse from this amplifier appearing on line 55 is a voltage signal whose amplitude is proportional to the total energy of the scintillation event. This total energy signal is designated by the letter E and is available at the output of summing amplifier 54 and at the point which is marked E in FIG. 1. Each total energy pulse is processed in a pulse height analyzer or window-type discriminator which is enclosed in the dashed line rectangle marked 56. There is a lower energy level discriminator comprising a threshold amplifier 57 and a one-shot multivibrator (OSMV) 58 and an upper level discriminator comprised of a threshold amplifier 59 and an OSMV 60. Threshold amplifier 57 is essentially a comparator that has an input 61 for the E pulse and another input 62 for a reference voltage that is obtained with a variable voltage divider 63. Any incoming E pulse that exceeds the threshold of amplifier 57 triggers OSMV 58 to produce a z pulse 51 which, unless it is inhibited by action of the upper level discriminator, is delivered by way of line 52 to cathode ray tube control grid. 50. Threshold amplifier 57 discriminates against all energy pulses that are below the lower energy level of the window.

The other threshold amplifier 59 also receives all total energy or E pulses. Any E pulse whose energy level goes above the upper window level triggers OSMV 60 which grounds the output of lower level discriminator and hence inhibits production of a z pulse 51 if the total energy is above the upper limit. Threshold amplifier 59 also has an input from a variable voltage divider 64 which permits setting the upper window limit. Thus, it will be seen that with this conventional arrangement the amplitude of the z pulses 51 will be constant regardless of the amplitude of the total energy pulse, E, as long as the peak is within the discriminator window.

The graphs in FIG. 3 will be considered before the exemplary circuit in FIG. 2 for deemphasizing the effect of Compton scattered radiation is discussed in detail. The upper part of FIG. 3 is a plot of the gamma ray energy spectrum which is typically intercepted by the gamma camera versus the percentages of scintillation events that are likely to have a particular energy level in the spectrum. Gamma ray emissions which have appropriate energy for being detected as valid events are those which fall within the discriminator or pulse height analyzer window. The lower energy level of the discriminator is indicated by the line marked 70 and LL and the upper level of the discriminator is indicated by the line marked 71 and UL. The peak percentage of events occurs at the energy level indicated by line 72 in this particular illustration. Below the lower window level 70 there is a substantial amount of Compton scatter events 73, shown shaded, which must be discriminated against or not detected by the gamma camera.

Some Compton scatter events occur within the window and are indicated by the shaded region marked 74. This radiation manifests itself as an addition to the energy events 75 that fall within the window limits LL and UL. The contribution to the total number of events due to Compton modified radiation in the acceptable part of the energy spectrum is indicated by the shaded area 76 in the plot. The contribution to the total number of events due to Compton scattering 76 decreases and may finally disappear where the peak number of events along the energy spectrum at 72 is approached and reached. As indicated earlier, prior practice has been to produce a z pulse of constant amplitude any time an event falling in the window between upper and lower energy levels UL and LL is detected. In accordance with the invention, the amplitude of the z pulses is variable and proportional to gamma photon energy in the lower energy part of the spectrum between the lower level window 70 and the energy peak 72. For energies at and beyond peak 72, the z pulses produced by the new deemphasizer are set at a maximum but definitely limited and constant amplitude.

In the lower part of FIG. 3, a variety of pulse heights 77 are shown. These are the summations of the energies of all the pulses produced by all of the PM tubes in response to detection of a scintillation event in scintillator crystal 12. The illustrative pulses 78–82 are voltage signals which are proportional to the total energy in the scintillation event. The peak of pulse 78 is below the lower window level 70 and is discriminated against. Pulses having energies falling within the window, such as those marked 79, 80 and 81 are detected. Pulses such as 82 which have energy above the upper discriminator window level are not detected.

Refer now to the illustrative Compton scatter deemphasizer circuit shown in FIG. 2. The input terminal to this circuit is marked 85 and it receives the total energy signal, E, over line 55 from summing amplifier 54 output instead of having it go to the type of pulse height analyzer 56 to which it goes in FIG. 1. The total energy signal is supplied through an input resistor 86 to the non-inverting input of a threshold amplifier 87 which has the properties of a comparator. This amplifier acts as the lower energy level discriminator. The threshold of amplifier 87 may be set by adjusting the bias voltage on its non-inverting input. This bias voltage is obtained with a voltage divider comprised of resistors 88 and 89 and a filter capacitor 90. The bias potential on the inverting input of threshold amplifier 87 can be varied or set by selecting one of a group of resistors 91 with a rotary switch contact 92. A potentiometer could be substituted for resistor network 91. A variable feedback resistor 83 is provided for setting the gain of the threshold amplifier or comparator 87. Any total energy pulse, E, which is above the threshold or lower discriminator level to which threshold amplifier 87 is set, will produce a pulse on the output 93 of threshold amplifier 87. These are essentially pulse peaks whose amplitudes are proportional to the amount by which the total energy input signal peak exceeds the lower window level. A typical pulse 94 is shown adjacent output branch line 95. By way of example, this might correspond with a pulse that just exceeds lower threshold level by a small amount such as pulse peak 79 in FIG. 3. In FIG. 2, output pulses such as 94 are fed through a resistor 96 to the non-inverting input of a summing amplifier 97. The summing point is marked 98 and it has another summing resistor 99 connected to it.

Every energy pulse peak 94 is supplied to a gate such as one-shot multivibrator 100 (OSMV) whose Q output, in this example, is at a logic high when there is no input pulse and switches to a logic low upon occurrence of an input pulse. The Q output is connected through a biasing resistor 101, in parallel with a filter capacitor, to the base-emitter circuit of a transistor 102 which is conducting when Q is high. When an energy pulse peak in excess of the lower window level UL, such as peak 94, is delivered from threshold amplifier 87, the Q output of the OSMV 100 switches to low level and turns off transistor 102. Transistor 102 has a collector resistor 103 which is supplied with a positive voltage. It will be evident that when transistor 102 turns off, its collector voltage will go to a logic high and a positive going pulse will be coupled through summing resistor 99 to summing point 98. The square wave pulses provided from the collector of transistor 102 under the control of OSMV 100 are constant amplitude pulses and are called the basic z pulse herein. A summing amplifier 97, having a feedback resistor 106, is operative to add the peak energy representative pulses 94 from threshold amplifier 93 to the basic z pulse produced by OSMV 100 and these summed pulses appear on the output line 104 of amplifier 97. An exemplary output pulse is shown adjacent line 104. It comprises the basic z pulse 105 and the added energy pulse 94. Z pulse output line 104 in FIG. 2 would connect to unblanking signal control grid 50 in place of line 52 of the FIG. 1 embodiment.

It should now be apparent that low total energy peaks which exceed the lower window or threshold by a small amount, such as energy peak 79 in FIG. 3, are in that part of the energy spectrum where there is substantial Compton modified radiation so these peaks now add little peak signals 94 to the basic z pulse 105. The result is that the light spots produced on the display screen are less than maximum brightness for energies in the range where Compton radiation is prevalent. As will be discussed more fully later, as total energy pulses E, such as those marked 80 and 81 in FIG. 3, exceed the lower window level by progressively greater amounts, correspondingly larger amplitude pulse peaks 94 are added to the basic z pulse so the light spots on the screen for these energies are brighter as they should be since there is also less Compton radiation to be deemphasized. When total energy pulses have the energy of the pulse 81 in FIG. 3, they are out of the part of the spectrum where Compton radiation exists, such as near and beyond abscissa 72. Threshold amplifier 87 saturates at this level and adds the maximum permissible signal 94 to the basic z pulse 105 so all more energetic pulses result in spots of uniform highest brightness being produced on the display screen 36.

Every incoming total energy signal at input terminal 85 in FIG. 2 is also fed through an input resistor 110 to the non-inverting input of a comparator amplifier 111 which establishes the upper window level for energy discrimination. It inhibits production of any z pulse if the energy level exceeds an upper limit of the window. The inverting input of amplifier 111 is biased with a resistor 112 to set its level. There is a filter capacitor 113 in the circuit. Any total energy signal, E, which exceeds the upper level setting of amplifier 111 causes its output signal on output line 114 to switch from a logic low to a logic high signal in this example. This signal is the input to a one-shot multivibrator 115 whose $\overline{Q}$ output is at a logic low level in the absence of high signal on line 114. The $\overline{Q}$ output is coupled through a resistor 116 to the base-emitter circuit of a transistor 117. The collector of this transistor is normally high by virtue of the voltage applied through collector resistor 103. When the total energy signal exceeds the upper level setting of amplifier 111, the $\overline{Q}$ output switches to a logic high and turns on transistor 117. This grounds or reduces the collector voltage of transistor 117 to near 0 and, essentially grounds the z pulse components which would otherwise be coupled to summing amplifier 97. In other words, when the total energy of a gamma ray absorption event exceeds the upper window level of the discriminator, the z pulse is inhibited and the cathode ray tube is not unblanked so no light spot will be produced on the cathode ray tube screen for the particular overenergetic signal.

Figure 4:
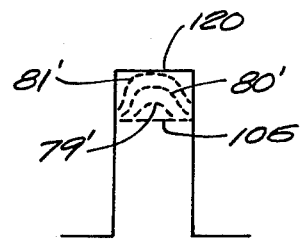
FIG. 4 shows the type of z pulses which are obtained with the deemphasizer.

Refer to FIG. 3 again for looking at the total effect. Consider a gamma ray emission or a pulse, such as the one marked 79, which has just enough total energy to exceed the lower window level 70 of the discriminator. It will cause a relatively low level peak 94 output from amplifier 87 in FIG. 2. The energy of pulse 79 falls within that part of the spectrum where there is a substantial amount of Compton scattered radiation 76 present. Hence, in accordance with the invention, the Compton effect is deemphasized by adding only a small signal 94 to the basic z pulse signal. In FIG. 4, the basic z pulse signal amplitude is indicated by the dashed line marked 105. The amount of signal added, due to relatively low energy pulse 79 is marked 79'. The summation of basic pulse 105 and pulse 79' constitutes the entire z pulse for this particular total energy. Going back to FIG. 3, another total energy pulse 80 is to be considered. Its peak falls in that part of the spectrum where Compton scattered radiation energy is rapidly declining. Hence, most of the detected signal is valid and an increasingly larger output pulse is delivered from threshold amplifier 87. FIG. 4 shows the resulting pulse 80' which is added to the basic z pulse 105 to produce a higher amplitude z pulse and, thus, cause a brighter light spot to appear on the screen of the cathode ray tube.

Any total energy pulses, such as the one marked 81 in FIG. 3, which reach the peak point 72 in the energy spectrum and fall within the window, of course, result in output pulses from threshold amplifier 87 which are near maximum. In other words, when the energy in any total energy pulse reaches the level at about the peak point in the energy spectrum, amplifier 87 is driven into saturation, as previously explained, so that pulses having greater energy will not cause any change in the amplitude of the output pulse from amplifier 87. The typical total energy pulse 81 in FIG. 3 results in the addition of signal 81' to the basic pulse 105 in FIG. 4. In respect to FIG. 3, any total energy pulses which exceed the peak point 72 drive threshold amplifier 87 into saturation so that the maximum z pulse amplitude ever achieved is at the level indicated by the line 120 in FIG. 4. Of course, total energy signals that have such high amplitude as to go beyond the upper window level 71, such as pulse 82 in FIG. 3, have no effect on the z pulse because z pulses are inhibited by virtue of transistor 117 turning on when such energy levels are encountered.

Figure 5:
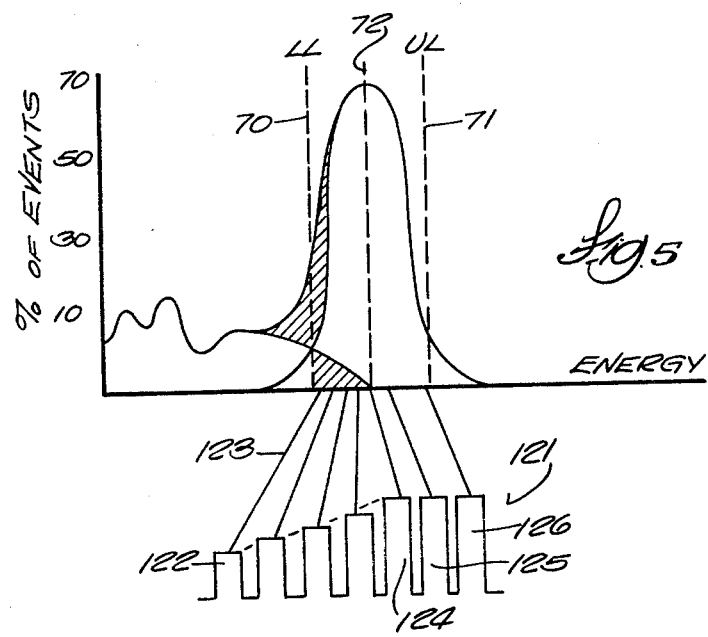
FIG. 5 is another plot of the percentage of events at particular energies versus energy, this plot being used for additional explanation of the invention.

FIG. 5 exemplifies the functional aspects of the invention in another way for the sake of clarity. The upper portion of the FIG. 5 graph may be considered identical to the upper portion of the FIG. 3 graph. A series of z pulses 121 are depicted below the energy graph. The first z pulse 122 has resulted from a gamma ray emission and absorption event which has energy falling in that part of the spectrum where Compton scattered radiation is significant and, hence, the amplitude of z pulse 122 is just slightly greater than the basic z pulse amplitude. The light lines, such as the one marked 123, go back to the point on the energy spectrum or abscissa of the plot which is indicative of the total energy of the particular event. One may see how the z pulses increase in amplitude until a certain energy level 72 where there is no substantial Compton effect results in a maximum amplitude z pulse 124. Any z pulses resulting from events which have a total energy above the energy indicated by the line 72 result in z pulses such as 125 and 126 which are no greater in amplitude than z pulse 124. From the foregoing, it should be evident that in the part of the energy spectrum where the Compton scatter is greatest, the z pulses have the least amplitude and the corresponding points on the screen have the least brightness and in the part of the energy spectrum where Compton scatter is insignificant, the points are all uniformly bright.

Various amounts of Compton scattered radiation may be present with different isotopes so the compensation for Compton radiation may be adjusted accordingly. In the FIG. 2 circuit, the proper compensation can be made by adjusting the gain of threshold amplifier 87 up or down in accordance with the intensity of the Compton radiation.

Figure 6:
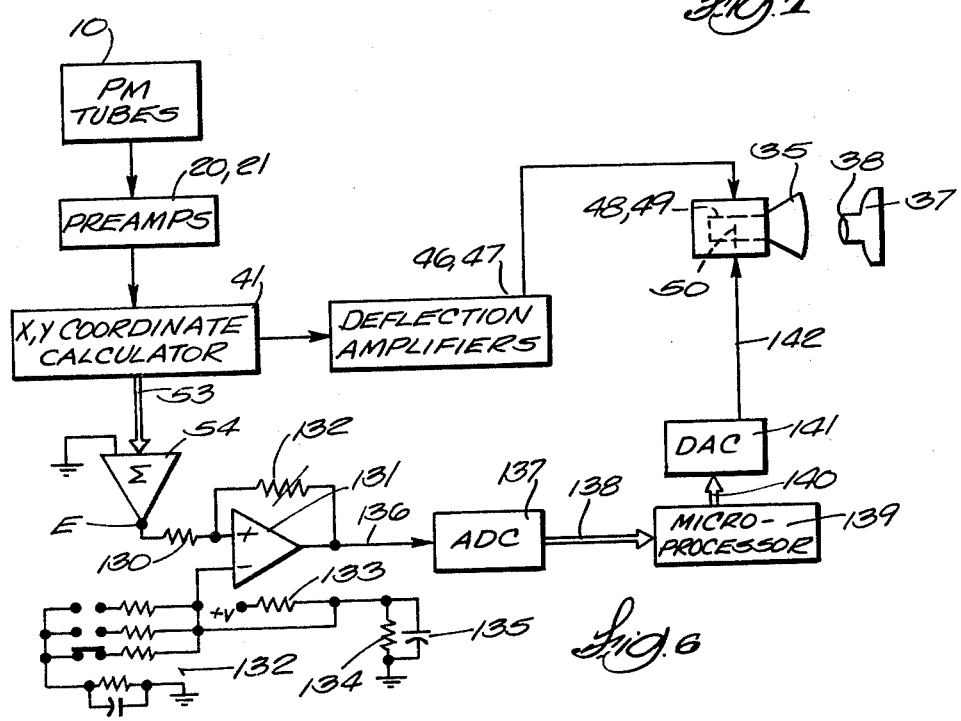
FIG. 6 is a block diagram of a system for accomplishing deemphasis with digital techniques instead of the analog technique illustrated in FIG. 2.

Those skilled in the art will now appreciate that Compton radiation deemphasis can be implemented with electronic circuitry that differs from the circuit illustrated in FIG. 2. For example, instead of processing the signals due to Compton radiation photons and valid direct photons as analog signals, the processing could be done with digital circuitry as well. FIG. 6 is a block diagram of a system which accomplishes Compton radiation deemphasis using digital techniques. Parts of the circuit are conventional and are comparable to the circuit in FIG. 1. Such parts are given the same reference numerals. Thus, there is the usual array of PM tubes 10 as the input to the gamma camera. The pulse outputs of the PM tubes are processed in preamplifiers 20, 21 and so forth, and the x and y coordinates of each scintillation event are determined in a calculator 41. The x and y coordinate signals are amplified in deflection amplifiers 46 and 47 and supplied to deflection coils 48 and 49 of a cathode ray tube 35. As in the previously described embodiment of the Compton scatter deemphasizer, z pulses are supplied to the control grid 50 of cathode ray tube 35 to unblank it and produce a light spot on its screen in the FIG. 6 embodiment.

In FIG. 6, as in the previous embodiment, each of the analog signals representing the energy signals from the PM tubes are fed from calculator 41 to the summing amplifier 54 whose output signal is designated by E and represents the total energy of a scintillation event.

In FIG. 6, the total energy signal, E, is fed through input resistor 130 to an input of a threshold sensitive comparator amplifier 131 which has a variable feedback resistor 132 for setting its gain. The threshold level or bias of comparator 131 is set with a switchable resistor network 132 which has circuit elements arranged comparably to network 91 in FIG. 2. There is also a divider comprised of resistors 133 and 134 and a filter capacitor 135 for supplying the bias voltage to the network.

Comparator 131 is set so that it will produce an analog output signal on its output line 136 that corresponds with the total energy signal E which is fed into it provided the energy level of E is above the threshold which has been set with bias circuit 132. The threshold actually corresponds with the lower level, LL, of a window or the lowest total energy signal that is acceptable. Comparator 131 does not become saturated within the range of energy levels of valid scintillations; that is, comparator 131 does not set the upper window limit, UL, of E signals.

All of the total energy signals E are supplied by way of threshold comparator amplifier output line 136 to an analog-to-digital converter marked ADC and 137 where the successive E signals are converted to digital values. These digital signals are supplied by way of a multiple bit data bus 138 to a microprocessor 139 or other suitable computing system. As will be explained, microprocessor 139 determines what the amplitudes of the z pulses should be and these amplitudes, of course, will vary depending on where the E pulse energy peaks fall in the scintillation energy spectrum, as depicted in FIG. 3. The calculated values of the z pulses in digital form are fed from microprocessor 139 by way of a multiple bit bus 140 to a digital-to-analog converter (DAC) 141 where they are converted to analog signals which are fed to the unblanking grid 50 of cathode ray tube 35 by way of line 142.

The digital value corresponding with the upper energy level limit for E, that is, the UL value in FIG. 3, is stored in microprocessor memory. A digital value corresponding with the energy of E pulses at level 72 in FIG. 3 is also stored. Level 72 is designated the reference level, RL, in connection with the digital method of Compton scatter deemphasis which is presently being described. As has been explained and as is evident in FIG. 3, there is progressively less Compton scatter proceeding away from the lower E level or limit toward RL and practically no Compton scatter above the RL level to the upper energy limit UL.

The microprocessor compares the energy signals from ADC 137 with the stored UL values. If the incoming total energy signal E is greater than UL in amplitude, the microprocessor will not output a digital z pulse signal to DAC since the energy is too great to be accepted.

If the comparison shows that the E signal is below the UL, the microprocessor continues in its program to determine if the E value lies between UL and the reference level, RL, and where it lies in this range which includes Compton scatter and it also determines if it lies in the energy range between RL and UL where there is to be no Compton scatter deemphasis. Thus, the microprocessor compares the E signal value with the RL value. If E is equal to or greater than RL, and less than UL, the microprocessor causes the DAC 141 to send the highest amplitude z pulse, called a 2K level pulse for reasons which will become clear, to the unblanking grid 50 of the cathode ray tube so the brightest light spot will be developed on its screen. On the other hand, if the comparison shows the E pulse has an energy level between LL and RL, the z pulse level will be prorated or adjusted according to where the E pulse is in the Compton scatter range in accordance with a selected deemphasis formula such as the formula $K+1/(RL-E)$ where K is the basic z pulse level and the added quantity is the deemphasis factor.

Assume for example that the reference level, RL, has a stored value of 10 units. An E signal very near the energy level of RL would be interpreted, let us say, by the microprocessor as having a value of 9 so $RL-E=10-9=1$. E may change by increments of 1 down to near the LL level where $E=1$ and $RL-E=10-1=9$. The reciprocals of $RL-E$ are calculated so $K/(RL-E)$ ranges from $1/9K$ to $1/1K$. The reciprocals are the correction factors which are to be added to the basic z pulse level. Hence, z amplitude $=K+K/(RL-E)$.

The computer or microprocessor software essentials are:
00: READ E
01: COMPARE RL & E, IF E < RL GO TO 10; IF E > RL GO TO 20; IF E > UL GO TO 30.
10: SUBTRACT $RL-E$.
11: $K/(RL-E)$
12: ADD CONSTANT K.
13: OUTPUT Z VALUE TO DAC 141.
20: ADD K + K.
21: OUTPUT TO DAC 141.
30: IGNORE E.
31: OUTPUT 0000.

Figure 7:
FIG. 7 is a diagram used to described the FIG. 6 embodiment of the Compton scatter deemphasizer.

The operation is summarized pictorially in FIG. 7.

Although two systems for implementing Compton scatter deemphasis have been described in considerable detail, such description is intended to be illustrative rather than limiting, for the invention may be variously embodied and is to be limited only by interpretation of the claims which follow.

I claim:

1. A Compton scattered photon deemphasizer device for a gamma camera system including a scintillator which scintillates where there are gamma photon absorption events caused by photons having a spectrum of energies residing between lower and upper energy limits and including energies indicative of some photons having lost energy by having experienced Compton scattering, an array of photodetectors optically coupled to said scintillator and operative to produce electric signals, respectively, having values depending on the physical relation of the photodetector to an event and on the energy of the event, means for summing said signals and for producing a total energy signal proportional to the total energy of an event, means for producing coordinate signals corresponding with the coordinates of said events in the scintillator, cathode ray tube display means having a screen and including means controlled by said coordinate signals to determine corresponding coordinates of respective events on said screen, said tube including a control electrode to which z pulses are applied for enabling said tube to display events on said screen, said deemphasizer device having input means for receiving successive total energy signals and z pulse output means coupled with said cathode ray tube control electrode, means in said deemphasizer device for determining the peak energy level of each total energy signal falling between said lower and upper limits of said spectrum, means responsive to said peak level being determined by producing a z pulse proportional in amplitude to the energy level of the peak for peaks representative of energies greater than said lower energy limit and less than or equal to a predetermined higher energy level in the part of the spectrum where significant Compton scattered photons exist and by producing constant amplitude z pulses for the part of the spectrum falling between said predetermined level and said upper energy limit.

2. The deemphasizer device as in claim 1 including:

comparator means having an output terminal and having an input terminal coupled to said input means and having means for supplying a reference signal for comparison with said total energy signals, said comparator means being operative to produce an output signal proportional in amplitude to the amount by which the total energy signal input exceeds a threshold level determined by said reference signal, said threshold level corresponding with said lower limit of a window bounded by said lower and upper limits in said spectrum, means responsive to output signals from said first comparator means by generating basic z pulses of constant amplitude, summing means having said output means which is coupled to said display tube control electrode and being operative to sum said signals from said first comparator means and said basic z pulse to produce a z pulse on its output terminal having an amplitude corresponding with the amplitude of said total energy signal, and means responding to said total energy signals exceeding a predetermined upper energy limit by inhibiting production of z signals.

3. The deemphasizer device as in claim 1 including:

comparator means having input means for receiving said total energy signals and having output means, said comparator means being operative to produce analog output signals for total energy signals that exceed a predetermined lower energy limit, means for converting said analog signals to corresponding first digital signals, computer means having input means for said first digital signals and having output means for second digital signals, said computer means being operative: to produce second digital signals having a minimum basic amplitude in correspondence with first digital signals that result from the lowest energy level total energy signals; to produce increasingly larger second digital signals for correspondingly increasing first digital signals until a predetermined energy level in said spectrum is reached; to produce constant maximum value second digital signals after said predetermined energy level is reached; and, to produce no second digital signals when a predetermined upper energy level limit is reached, digital-to-analog converter means having input means for said second digital signals and having output means which are coupled to said display tube control electrode, said converter means being operative to convert said second signals to analog z pulses.

4. A gamma camera including a scintillator for producing scintillations in response to absorbing gamma ray photons emitted from a body where the photons have a spectrum of energies and where photons between lower and upper energy limits in a part of the spectrum are acceptable for developing an image and some Compton scattered photons contribute to the spectrum primarily in the region between the lower limit and another higher energy level, a plurality of photodetectors optically coupled to said scintillator and responsive to occurrence of scintillations by producing electric analog signals proportional to energy, means for summing said signals to produce a total energy signal, means for producing signals corresponding with the coordinates of a scintillation, and cathode ray tube display means having a control electrode to which z pulses are applied to unblank the tube and produce a light spot at corresponding coordinates, and a Compton scattered photon deemphasizer comprising:

threshold amplifier means having input means for receiving said total energy signals and having output means, said amplifier means being operative to produce output pulse signals proportional in amplitude to the amount by which said total energy signals exceed said lower energy limit and increasing in amplitude progressively from said lower limit toward said another energy level in the spectrum as said Compton scattered photons become less prevalent, gate means for producing basic z pulse signals of constant amplitude simultaneously with and in response to occurrence of said output pulses, summing means for summing said output pulse signals and said basic z pulse signals, the summed signal constituting the total z pulse being coupled to said cathode ray tube control electrode.

5. The deemphasizer as in claim 4 including means responding to total energy signals which are greater than said upper energy limit by inhibiting production of z pulses for such total energy signals.

6. The deemphasizer as in claim 4 wherein said gate means is a one-shot multivibrator having input means for being triggered by said output pulses from said threshold amplifier means.

7. A gamma camera including a scintillator for producing scintillations in response to absorbing gamma ray photons emitted from a body where the photons have a spectrum of energies and where photons between lower and upper energy limits in a part of the spectrum are acceptable for developing an image and some Compton scattered photons contribute to the spectrum primarily in the region between the lower limit and another higher energy level, a plurality of photodetectors optically coupled to said scintillator and responsive to occurrence of scintillations by producing electric analog signals proportional to energy, means for summing said signals to produce a total energy signal, means for producing signals corresponding with the coordinates of a scintillation, and cathode ray tube display means having a control electrode to which z pulses are applied to unblank the tube and produce a light spot at corresponding coordinates, and A Compton scattered photon deemphasizer, threshold amplifier means having input means for receiving said total energy signals and having output means, said threshold amplifier means being operative to produce analog output signals proportional in amplitude to the amount by which said total energy signals exceed said lower energy limits, analog-to-digital converted means operative to convert said analog output signals which are proportional to total energy to corresponding digital signals, computer means programmed to detect the magnitude of said digital signals and: to produce a digital value corresponding with a minimum amplitude z pulse for total energy representative signals at or near said lower energy limit of said part of the spectrum; to produce increasingly larger amplitude digital values progressively from said lower energy limit to said another higher energy level; and, to produce constant maximum amplitude digital values for total energy representative signals between said higher energy level and said upper limit, digital-to-analog converter means for converting said digital values corresponding with z pulses to analog signals, and means for coupling said analog z signals to said control electrode of said cathode ray tube.

* * * * *